United States Patent
Galin et al.

[19]

[11] Patent Number: 6,143,028
[45] Date of Patent: *Nov. 7, 2000

[54] MEDICAMENT COATED REFRACTIVE ANTERIOR CHAMBER OCULAR IMPLANT

[76] Inventors: Miles A. Galin, 345 E. 37th St., 3rd Flr., New York, N.Y. 10016; Joseph C. Salamone, 2202 NW. 62nd Dr., Boca Raton, Fla. 33496; Stanley C. Israel, 675 West St., Carlisle, Mass. 01741

[*] Notice: This patent is subject to a terminal disclaimer.

[21] Appl. No.: 09/063,624

[22] Filed: Apr. 20, 1998

Related U.S. Application Data

[63] Continuation of application No. 08/815,895, Mar. 12, 1997, Pat. No. 5,994,753, which is a continuation of application No. 08/193,160, Aug. 25, 1994, Pat. No. 5,652,014, said application No. PCT/US92/06818, Aug. 13, 1992, is a continuation-in-part of application No. 07/745,927, Aug. 16, 1991, abandoned.

[51] Int. Cl.$^7$ ............................................... A61F 2/16
[52] U.S. Cl. ............................................. 623/6.62; 623/6.6
[58] Field of Search .............................. 623/5, 6; 427/2.1, 427/2.24, 536

[56] References Cited

U.S. PATENT DOCUMENTS

| | | |
|---|---|---|
| 598,861 | 2/1898 | Delano . |
| 839,084 | 12/1906 | Fleming . |
| 3,766,167 | 10/1973 | Lasker et al. . |
| 4,170,043 | 10/1979 | Knight et al. . |
| 4,174,543 | 11/1979 | Kelman . |

(List continued on next page.)

FOREIGN PATENT DOCUMENTS

| | | |
|---|---|---|
| 1516111 | 10/1989 | U.S.S.R. . |
| 1546084 | 2/1990 | U.S.S.R. . |
| 2165456 | 4/1986 | United Kingdom . |
| 9103990 | 4/1991 | WIPO . |

OTHER PUBLICATIONS

VMG Ferguson et al. "Continued breakdown of the blood aqueous barrier follow cataract surgery", British Journal of Opthamology, vol. 76, pp. 453–456 (1992).
"Cell loss prompts redesign of ACL for phakic myopia".
"The Eye" by G. Wstheimer, in Medical Physiology, Thirteenth edition, edited by V.B. Mountcastle, vol. 1, pp. 440–442.
Brochure of Kabi Pharmacia (Uppsala, Sweden).
"Surface–modified IOL's: A new approach to cataract surgery", published by Pharmacia AB (Uppala, Sweden).
Abstracts of WO 9007914, DE 2128527 and DE 2725219.

(List continued on next page.)

*Primary Examiner*—Paul B. Prebilic
*Attorney, Agent, or Firm*—Baker Botts LLP

[57] ABSTRACT

A minus power anterior chamber ocular implant for placement in the anterior chamber of a phakic eye having an anatomic lens in situ comprises a negative artificial refracting lens having at least one concave surface, a surface coating which comprises a compatible sulfated polysaccharide medicament coating, such as heparin, and having a structure which positions the artificial lens in the anterior chamber of the eye to prevent contact between the implant and the anatomic lens. The implant compensates for refractive errors or creates a specific refraction to assist in visual function and has increased biocompatibility in the anterior chamber of the eye, thereby preventing or mitigating detrimental effects typically associated with the implantation of an uncoated refractive anterior chamber implant in the eye. A method of preparing such a minus power anterior chamber ocular implant comprises first exposing an uncoated implant to a plasma to generate a plasma-treated implant having a surface containing amines, carboxylic acids, active free radicals or passive free radicals, and thereafter bonding the medicament to the plasma-treated implant surface. A method of treating myopia comprises surgically implanting and anchoring the implant in the phakic eye to compensate for refractive errors.

12 Claims, 1 Drawing Sheet

U.S. PATENT DOCUMENTS

| | | |
|---|---|---|
| 4,240,163 | 12/1980 | Galin . |
| 4,249,271 | 2/1981 | Poler . |
| 4,343,050 | 8/1982 | Kelman . |
| 4,437,194 | 3/1984 | Hahs . |
| 4,448,718 | 5/1984 | Yannas et al. . |
| 4,478,981 | 10/1984 | Arkles . |
| 4,502,162 | 3/1985 | Gerhard et al. . |
| 4,504,981 | 3/1985 | Walman . |
| 4,613,517 | 9/1986 | Williams et al. . |
| 4,676,792 | 6/1987 | Praeger . |
| 4,681,585 | 7/1987 | Sanyo et al. . |
| 4,687,484 | 8/1987 | Kaplan . |
| 4,713,244 | 12/1987 | Bawa et al. . |
| 4,716,154 | 12/1987 | Malson et al. . |
| 4,731,080 | 3/1988 | Galin . |
| 4,816,032 | 3/1989 | Hetland . |
| 4,826,478 | 5/1989 | Schocket . |
| 4,840,626 | 6/1989 | Linsky et al. . |
| 4,871,363 | 10/1989 | Kelman . |
| 4,955,901 | 9/1990 | Nishiguchi et al. . |
| 5,071,432 | 12/1991 | Baikoff . |
| 5,080,924 | 1/1992 | Kamel et al. . |
| 5,258,025 | 11/1993 | Fedorov et al. . |
| 5,652,014 | 7/1997 | Galin et al. ............................ 427/2.24 |
| 5,944,753 | 8/1999 | Galin et al. .................................. 623/6 |

OTHER PUBLICATIONS

Piera Versura, B.S.D. et al., "Ultrastructure of cells cultured onto various intraocular lens materials" J. Cataract Refract Surg., vol. 18, pp. 58–64.

Bjorn Lundgren, Ph.D., "Inflammatory response in the rabbit eye after intraocular implantation with poly(methyl methacrylate) and heparin surface modified intraocular lenses" J. Cataract Refract. Surg., vol. 18, pp. 65–70, (1992).

Bo Philipson M.D., "Heparin surface modified intraocular lenses Three–month follow–up of a randomized, double–masked clinical trial", J. Cataract Refract Surg., vol. 18, pp. 71–78, (1992).

Lawrence M. Fisher, "An Implant That Corrects the Cornea's Curvature", Tech. Notes N.Y. Times Business Section, May (1991).

"Minus Power Anterior Chamber Lenses for High Myopia" in Opthamology alert, vol. 1 No. 11, pp. 41–42 (Nov. 1990).

"Heparin–modified Surface Looks Promising in IOL Clinical Trials" in Opthamology Times, Nov. 1, p. 54 (1990).

Joseph Colin, M.D. et al., The Surgical Treatment of High Myopia: Comparison of Epikeratoplasty Keratomileusis and Minus Power Anterior Chamber Lenses, Refractive & Corneal Surgery, vol. 6, pp. 245–260, (1990).

R. Larsson et al. "Intraocular PMMA Lenses Modified With Surfact–immobilized Heparin: Evaluation of Biocompatibility in vitro and in vivo." Biomaterials 10:511–516 (1989).

R. Larsson et al. "The Search for Thromboresistance Using Immobilized Heparin" Ann. N.Y. Acad. Sci. 516: 102–115 (1987).

Kaufman et al., "Corneal Endothelium Damage with Intraocular Lenses: Contact Adhesion Between Surgical materials and Tissue" vol. 198 Science pp. 525–527, Nov. 4, 1977.

Katz et al., "Prevention of Endothelial Damage From Intraocular Lens Insertion" vol. 83 Trans. American Academy of Ophthalmol. Otolaryngol, pp. Op–204 to op–212, Oct. 7, 1976.

MEDICAMENT COATED REFRACTIVE ANTERIOR CHAMBER OCULAR IMPLANT

CROSS REFERENCE TO RELATED APPLICATIONS

This is a continuation of pending U.S. patent application Ser. No. 08/815,895, filed Mar. 12, 1997 now U.S. Pat. No. 5,994,753, which is a continuation of U.S. patent application Ser. No. 08/193,160, filed on Aug. 25, 1994, which issued as U.S. Pat. No. 5,652,014 on Jul. 29, 1997, which is a national phase application pursuant to 35 U.S.C. §371 of PCT/US92/06818, filed Aug. 13, 1992, which is a continuation-in-part of U.S. patent application Ser. No. 07/745,927, filed Aug. 16, 1991, now abandoned. The entire disclosure of each of the prior applications, Ser. No. 08/815,895, Ser. No. 08/193,160, which is a national phase application pursuant to 35 U.S.C. §371 of PCT/US92/06818, and Ser. No. 07/745,927, are incorporated by reference herein in their entirety.

BACKGROUND OF THE INVENTION

This invention relates to a medicament-coated minus power anterior chamber ocular implant for placement in a phakic eye to correct refractive errors such as myopia, a method of preparing such an implant and a method of using such an implant in a myopic phakic human eye.

It is well known to those skilled in the field of ophthalmology that there has previously been, and continues to be, a need for a successful anterior chamber ocular implant in the phakic eye to compensate for refractive errors such as high myopia or to create a specific refraction to assist in visual function. For example, U.S. Pat. No. 4,676,792 (Praeger) discloses the use of an uncoated anterior chamber minus power lens having a planar anterior-facing surface and a concave posterior-facing surface in the treatment of myopia. In addition, the recent use of uncoated implants as a surgical approach for patients having high myopia that is not satisfactorily corrected with spectacles or contact lenses has been attempted in France, as described in Colin et al., Refractive and Corneal Surgery, Vol. 6 (July/August 1990), pp. 245–51 and Baikoff et al., Refractive and Corneal Surgery, Vol. 6, (July/August 1990), pp. 252–60.

However, it has been acknowledged by those skilled in the art that there are significant risks involved in the use of such anterior chamber implants in the eye. For example, when such an implant is inserted into the eye, temporary or permanent adhesions of the implant to delicate intraocular structures may result, causing damage to these structures to ensue either immediately or over the long term. In addition, once the implant is in position, it may cause similar adhesions due to mechanical and/or chemical inflammation leading to fibrosis of a progressive nature and damaging of the intraocular tissue, thereby making subsequent removal of the implant a complex, dangerous surgical procedure. Other problems associated with such implants are cataract formation, secondary glaucoma, corneal edema, hyphema, and progressive endothelial cell loss, in addition to other complications.

As observed in Ophthalmology Alert, Vol. 1, No. 11 (November 1990), pp. 41–42, several American manufacturing companies which were preparing to begin clinical trials of anterior chamber ocular implants in the United States are now likely to abandon these studies, due to the attendant risks associated with the implants and the difficulty of obtaining approval of the federal Food and Drug Administration (FDA) for the use of the implants. In view of the foregoing, it would clearly be advantageous to employ a minus power anterior chamber ocular implant having a compatible medicament coating which would ameliorate and/or prevent the occurrence of the above-described problems associated with such implants.

It is also well known to those skilled in the art that an intraocular lens, when surgically inserted, is predominantly designed to replace a previously or simultaneously removed cataractous lens. However, although the implantation of intraocular lenses has constituted an appreciable surgical advance, such implantation has been known to cause immediate or late damage to the corneal endothelium, immediate or late inflammatory responses in the anterior and/or posterior segments of the eye, immediate or late secondary fibrosis and/or neovascularization, and other problems. In general, the phakic eye is more reactive than the aphakic eye, i.e. in the phakic eye, inflammatory reactions tend to be greater resulting in a concomitant increase in damage to the eye. Firstly, in the aphakic eye no lens pulls on the ciliary body; thus the ciliary body is in a "resting state" and tends to undergo some degree of atrophy. Therefore, an inflammatory response will be less in the aphakic eye. Secondly, the phakic eye has a shallower anterior chamber (i.e. the average antero-posterior depth is less) than the aphakic eye, and the iris has a greater surface area contacting the lens. Therefore, if an inflammatory reaction occurs in the phakic eye, there is a greater area of adherence of the iris to the anterior surface of the anatomic lens.

To overcome the above-described problems associated with the use of intraocular lenses to replace cataractous lenses, the use of intraocular lenses having various coatings has previously been disclosed. For example, U.S. Pat. No. 4,170,043 (Knight et al.) discloses coated intraocular lenses made of an acrylic resin having a coating to prevent adhesion of the intraocular lens to the corneal endothelium, the coating being polyvinylpyrrolidone, polyvinyl alcohol, hydroxypropyl cellulose, hydroxypropyl methylcellulose, dextran, hydroxyethyl starch, methylcellulose or guar gum. However, some of these coatings have been found to cause inflammatory reactions and have proven to be unsatisfactory in clinical practice.

West German patent application No. 2,556,665 discloses coated intraocular lenses wherein the coating is a silicon rubber, such as methyl or methylphenyl siloxane. U.S. Pat. No. 4,240,163 (Galin) discloses coated intraocular lenses wherein the coating is a compatible medicament such as sulfated polysaccharide. Also, intraocular lenses having a covalent attachment of heparin to a polyamine that is ionically adsorbed onto an intraocular lens surface have been disclosed in product literature of Pharmacia AB of Uppsala, Sweden entitled "Surface Modified IOLs: A New Approach to Cataract Surgery," pp.17–19.

A further risk involved in the use of such anterior chamber implants in the eye is the potential for the implanted lens to touch the cornea and/or to contact the anatomic lens and/or the iris with resultant complications. However, the above-mentioned possibility of the lens touching adjacent anatomical structures may be avoided or mitigated by vaulting the lens in such a way as to minimize the chance of this occurrence.

In view of the foregoing, it will be apparent to those skilled in the art that some of the problems associated with the use of anterior chamber ocular implants employed to correct refractive errors in the phakic eye differ from those associated with the use of intraocular lenses employed as replacements for surgically removed cataractous lenses. For example, the use of implants in the phakic eye may actually cause cataract formation in the natural lens which remains in situ, whereas the use of intraocular lenses in patients having cataract removal cannot induce such an effect, as the natural lens has been replaced by the intraocular lens.

It is one object of this invention to provide a minus power anterior chamber ocular implant for placement in the anterior chamber of an eye having an anatomic lens in situ. The implant comprises a negative artificial refracting lens having at least one concave surface, a surface coating comprising a compatible sulfated polysaccharide medicament, and means for positioning the artificial lens in the anterior chamber of the eye to prevent contact between the implant and the anatomic lens. The implant may be surgically implanted in the phakic eye to compensate for refractive errors, which avoids the concomitant problems described above. The implant may subsequently be removed from the eye, if necessary.

It is one feature of this invention that the coating may be bonded covalently, by ionic attraction, or hydrogen bonding to the surface of the implant. It is another feature of this invention that the sulfated polysaccharide coating may be selected from the group consisting of heparin, heparin sulfate, chondroitin sulfate, dermatan sulfate, chitosan sulfate, xylan sulfate, dextran sulfate, and sulfated hyaluronic acid. It is yet another feature of this invention that the coating may be additionally complexed with compounds having anticoagulation properties, such as antithrombin. It is yet another feature of this invention that the coating may additionally comprise one or more compounds capable of absorbing ultraviolet and other short wavelength radiation.

It is one advantage of the coated implant of this invention that it avoids attraction and minimizes the adherence of white blood cells, pigment granules and intraocular tissue to its surface. It is another advantage of this invention that it avoids stimulation of white cell activity and enzyme release which results in corneal endothelial destruction and dysfunction. It is yet another feature of this invention that cataract formation secondary to surgical trauma and/or short and long term inflammation may be minimized and/or avoided. It is yet another advantage of this invention that flare, white cells, vitreous reaction, cystoid macular edema, hyopyon, uveitis, and secondary glaucoma typically associated by those skilled in the art with the use of anterior chamber eye implants may be avoided.

It is another object of this invention to provide a method of preparing the above-described minus power anterior chamber ocular implant, wherein the implant avoids the above-discussed problems when it is surgically implanted into the eye, and may subsequently be removed from the eye if necessary.

It is one feature of the method of preparing such an implant that the coating may be bonded covalently, by ionic attraction, or hydrogen bonding to the surface of the implant. It is another feature of this method that the sulfated polysaccharide coating may be a selected from the group consisting of heparin, heparan sulfate, chondroitin sulfate, dermatan sulfate, chitosan sulfate, xylan sulfate, dextran sulfate, and sulfated hyaluronic acid. It is yet another feature of this method that the coating may be additionally complexed with compounds having anticoagulation properties, such as antithrombin. It is yet another feature of this method that the coating may additionally comprise one or more compounds capable of absorbing ultraviolet and other short wavelength radiation. It is yet another feature of this method that plasma-treating may first be used to treat an uncoated implant, and the medicament may thereafter be bonded to the plasma-treated surface.

It is one advantage of this method that it avoids attraction and minimizes the adherence of white blood cells, pigment granules and intraocular tissue to its surface. It is another advantage of this method that it avoids stimulation of white cell activity and enzyme release which results in corneal endothelial destruction and dysfunction. It is yet another feature of this method that cataract formation secondary to surgical trauma and/or short and long term inflammation may be minimized and/or avoided. It is yet another advantage of this method that flare, white cells, vitreous reaction, cystoid macular edema, hyopyon, uveitis, and secondary glaucoma typically associated by those skilled in the art with the use of anterior chamber eye implants may be avoided.

It is yet another object of this invention to provide a method of using the coated anterior chamber ocular implant of this invention in the treatment of myopia, wherein the implant is surgically implanted in the phakic eye to compensate for refractive errors, thereby advantageously avoiding the above-described problems. The implant may subsequently be removed from the eye, if necessary.

SUMMARY OF THE INVENTION

This invention is directed to a minus power anterior chamber ocular implant for placement in the anterior chamber of an eye having an anatomic lens in situ. The implant comprises a negative artificial refracting lens having at least one concave surface and a surface coating comprising a compatible sulfated polysaccharide medicament, and means for positioning the artificial lens in the anterior chamber of the eye to prevent contact between the implant and the anatomic lens.

The sulfated polysaccharide is preferably selected from the group consisting of heparin, heparan sulfate, chondroitin sulfate, dermatan sulfate, chitosan sulfate, xylan sulfate, dextran sulfate, and sulfonated hyaluronic acid, with heparin being particularly preferred. The heparin typically has a molecular weight in the range of about 2,500–15,000 daltons, preferably about 2,500–10,000 daltons, most preferably about 2,500–5,300 daltons. The coating is preferably bonded to the surface of the implant by means of ionic attraction, hydrogen bonding, or covalent bonding with covalent bonding being particularly preferred. The coating typically has a thickness in the range from about $1/100,000$ mm to $1/100$ mm, and constitutes from about $1/10,000\%$ to about $1/10\%$ by weight of the implant. The coating may additionally be complexed with compounds having anticoagulation properties such as antithrombin.

The coated minus power anterior chamber ocular implant of this invention is advantageous in that it may be implanted in the phakic eye to compensate for refractive errors, yet has increased biocompatibility in the anterior chamber of the eye, and thus avoids the problems typically associated with such implantation, including damage to the corneal endothelium, inflammatory responses in the anterior or posterior segments of the eve, particularly the formation of cataracts in the natural lens which is left in situ when the refractive anterior chamber implant is placed in the eye.

This invention is further directed to the method of preparing such a coated minus power anterior chamber ocular implant, the method comprising the steps of first exposing an uncoated surface of the implant to a plasma to generate a plasma-treated implant having a surface having constituents selected from the group consisting of amines, carboxylic acids, active free radicals, and passive free radicals, and thereafter bonding the sulfated polysaccharide medicament to the plasma-treated implant surface.

This invention is also directed to a method of treating myopia comprising surgically implanting and anchoring in the anterior chamber of a phakic eye the coated minus power anterior chamber ocular implant of this invention.

BRIEF DESCRIPTION OF THE DRAWINGS

The anterior chamber ocular implant of the present invention will hereinafter be described with reference, in part, to the accompanying drawings, in which.

DESCRIPTION OF THE PREFERRED EMBODIMENTS

Figure 1:
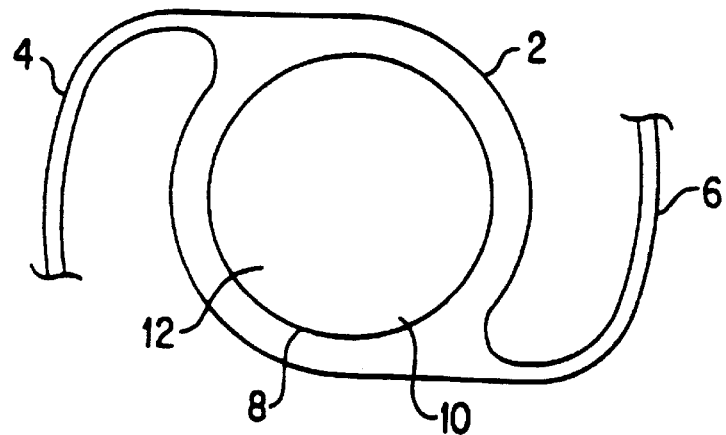
FIG. 1 is top plan view of one embodiment of an anterior chamber ocular implant in accordance with the present invention, wherein the negative refracting lens is biconcave.

This invention is directed to a minus power anterior chamber ocular implant for placement in the anterior chamber of an eye having an anatomic lens in situ. As used in this description and in the appended claims, the term "minus power anterior chamber ocular implant" refers specifically to a negative refracting lens surgically implanted in the phakic eye to compensate for and/or correct refractive errors, and specifically excludes intraocular lenses which are surgically inserted in the aphakic eye, such as are disclosed, for example, in U.S. Pat. No. 4,240,163 (Galin).

The negative refracting lens employed in the present invention has a lens shape with two refractive surfaces, at least one of which is concave, such that the combined refractive powers of the two surfaces is a minus or negative. Such lenses are typically employed to correct high myopia.

As discussed hereinabove, uncoated minus power anterior chamber ocular implants are well known to those skilled in the art. The optical portion of the implant employed in the present invention is preferably fabricated from compounds such as polymethyl methacrylate, poly-2-hydroxyethyl methacrylate, methyl methacrylate copolymers, siloxanylalkyl, fluoroalkyl and aryl methacrylates, silicone, silicone elastomers, polysulfones, polyvinyl alcohols, polyethylene oxides, copolymers of fluoroacrylates and methacrylates, and polymers and copolymers of hydroxyalkyl methacrylates, such as 2-hydroxyethyl methacrylate, glyceryl methacrylate, 2-hydroxypropyl methacrylate, as well as methacrylic acid, acrylic acid, acrylamide methacrylamide, N,N-dimethylacrylamide, and N-vinylpyrrolidone. Additionally, compounds which absorb ultraviolet or other short wavelength (e.g. below about 400 nm) radiation, such as compounds derived from benzotriazole groups, benzophenone groups, or mixtures thereof may be added to the monomers and/or polymers which constitute the anterior chamber ocular implant. Other compounds well known to those skilled in the art may also be used in fabricating the anterior chamber ocular implant employed in this invention.

It is well known to these skilled in the art that when positioning an implant within the anterior chamber of the phakic eye, it is important to avoid, inter alia, contact between the implant and the anatomic lens residing in the posterior chamber. In the present invention, haptics are integral to the optical portion of the implant, and position or "vault" the artificial lens in the anterior chamber of the eye to prevent such contact. The haptics may be of the same material as described above for the optical portion of the implant, or may be made of materials such as polypropylene. Haptics which may be employed in the implant of the present invention include haptics such as disclosed in U.S. Pat. No. 4,676,792 (Praeger), incorporated herein by reference.

Most minus power anterior chamber implants typically have an overall diameter of approximately 12–14 mm, if in a single piece of silicone or plastic, with an optical diameter of 4–6 mm. The center thickness and posterior radii of the optical portion of the implant typically varies according to the power desired and the material used. Such implants may typically weigh up to 25 mg in air, or about 0.5–4 mg in aqueous medium. Examples of uncoated anterior chamber ocular implants commercially available include those available from, for example, Domilens, Inc. of Lyon, France.

The sulfated polysaccharide medicament coating employed in conjunction with the anterior chamber ocular implant in this invention is preferably selected from the group consisting of heparin, heparan sulfate, chondroitin sulfate, dermatan sulfate, chitosan sulfate, xylan sulfate, dextran sulfate, and sulfated hyaluronic acid. Heparin is particularly preferred for use as the coating, with heparin having a molecular weight in the range of about 2,500–15,000 daltons. Commercially available heparin, which usually has a molecular weight of from about 12,000 to about 15,000 daltons, may lead to platelet agglutination. Consequently, lower molecular weight heparin (a derivative or fraction) may be more suitable in the range of molecular weight of from about 2,500–10,000, most preferably about 2,500–5,300 daltons and even somewhat higher. These low molecular weight heparins can be prepared by enzymatic hydrolysis or depolymerization of heparin with heparinase as disclosed, for example, by U.S. Pat. No. 3,766,167 (Lasker et al.), or by depolymerizing either heparin residues or commercial porcine or bovine heparin by reacting the heparin material with a blend of ascorbic acid and hydrogen peroxide, the reaction products then being isolated and fractionated by precipitation using an organic solvent, such as ethanol, methanol, acetone, or methyl ethyl ketone. Commercially available heparin may also be cleaved chemically using nitrous acid to yield lower molecular weight heparin, including heparin having a molecular weight in the range of about 2500–10,000 daltons, preferably 2500–5300 daltons.

In one preferred embodiment of this invention, as depicted in FIG. 1, the representative minus power anterior chamber ocular implant 2 has two haptics 4 and 6 integral to the negative artificial refracting lens 8, so that when implanted into the anterior chamber of the eye, the lens 8 is positioned to prevent contact between the implant 2 and the anatomic lens (not shown). In this view a first surface 10 of the negative refracting lens is visible, and the second surface 12 of the negative refracting lens resides directly below first surface 10. Both surfaces 10 and 12, as well as haptics 4 and 6 have a sulfated polysaccharide medicament coating 14 (not shown).

Figure 2:
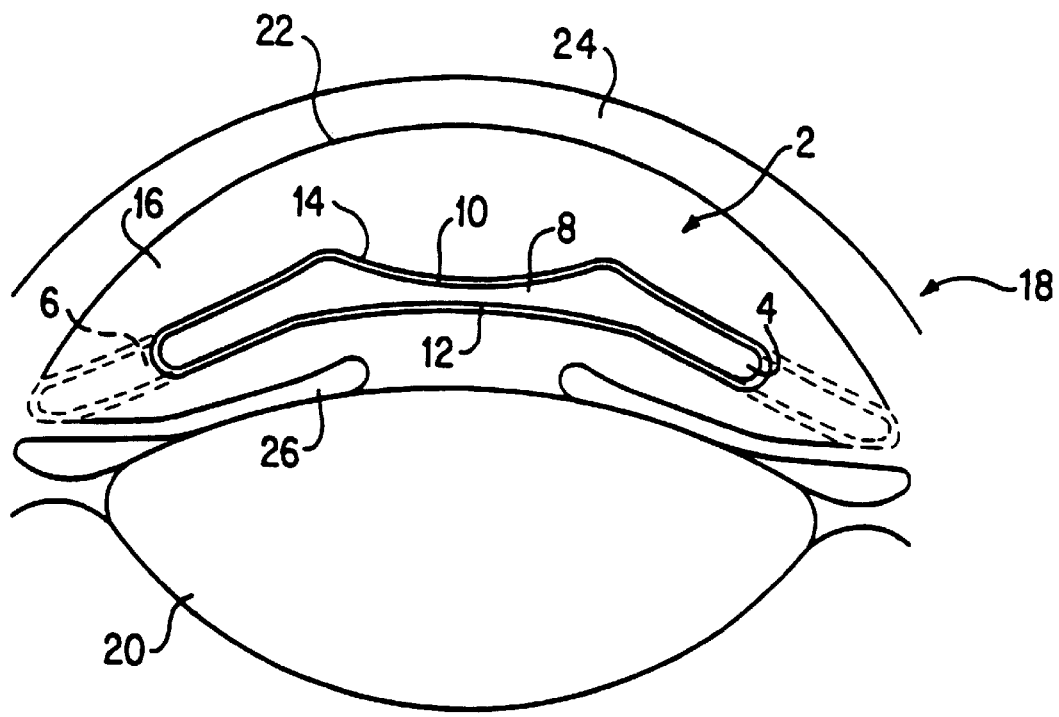
FIG. 2 is a side cross-sectional view of an eye containing the biconcave implanted anterior chamber ocular implant of FIG. 1.

As shown in FIG. 2, the implant 2 is implanted within the anterior chamber 16 of the eye 18, with the negative artificial refracting lens 8 positioned or vaulted by haptics 4 and 6 to prevent contact between the implant 2 and the anatomic lens 20. The implant 2 is also positioned to avoid contacting the corneal endothelium 22 behind the cornea 24, as well as the iris 26. In this embodiment, the first surface 10 is concave, and the second surface 12 is concave. In other embodiments of this invention, the first surface 10 may be concave, convex or planar, and the second surface 12 may be concave, convex or planar, with the proviso that at least one of surfaces 10 or 12 is concave. The first surface 10 and second surface 12, as well as the haptics 4 and 6, are coated with medicament coating 14. In FIG. 2, means for anchoring or fixing the haptics 4, 6 and implant 2 in the anterior chamber of the eye are not shown. Such means are well known to those skilled in the art; for example, the footplates disclosed in U.S. Pat. No. 4,676,792 (Praeger) may be employed in the present invention.

The coating of the present invention may be bonded to the surface of the implant by any method of bonding well known by those skilled in the art, preferably in such a manner that the coating is bonded to the surface of the implant by means of covalent bonding, ionic attraction, or hydrogen bonding, with covalent bonding being particularly preferred. In one particularly preferred embodiment of this invention, heparin is covalently bonded to the surface of the implant by means of an end-group attachment of heparin to the implant surface.

In another particularly preferred embodiment, the implant surface is first treated with a plasma to generate an amine-containing surface, a carboxylic acid containing-surface, or an active or passive free radical-containing surface, and heparin compounds or derivatives thereof is thereafter employed to coat the implant surface. In one embodiment, plasma treating is accomplished by setting the implant in a gaseous atmosphere such as an oxygen rarefied atmosphere, and subjecting the implant to an electromagnetic field for a given period of time. For example, in one embodiment the implant my be subjected from 1–10 minutes, say 2 minutes, to an electromagnetic field having a frequency in the range of 1–50 MHz, say about 10–15 MHz, with a corresponding power range of 10–500 W/cm$^2$, say about 100 W/cm$^2$.

In another embodiment, in accordance with techniques well known to these skilled in the art, plasma treating is accomplished by applying a voltage between electrodes wherein the uncoated implant resides between the electrodes in the presence of a gas, thereby causing a highly ionized gas to bombard the implant surface so as to cause the desired constituent (i.e. amine, carboxylic acid, active free radical, or passive free radical) to reside in the implant surface. The gas employed may comprise a carrier gas, either alone or in combination with other gases. The carrier gas may be any gas, but argon or air are preferred, with argon gas typically being used. The pressure of the gas is typically between 1.0 and 3,000 torr. Equipment which may be employed to achieve such plasma treating is well known to those skilled in the art, such as the equipment described in U.S. Pat. No. 4,780,176 (Sudarshan et al.) for plasma cleaning and etching a metal substrate, which is incorporated herein by reference. In the present invention, a power input to the electrode of 10–500 W may be employed to achieve a corresponding potential difference across the gap between the electrodes.

To generate an amine-containing surface, a plasma containing ammonia or a primary amine-containing material is used. A carboxylic acid-containing surface is generated by an oxidative reaction occurring at the surface or by having residual water in the plasma under inert conditions. In such an embodiment, argon is typically used as the carrier gas. Exposing the surface to argon gas plasma at sufficiently high power causes bond fission, yielding an active free radical-containing surface, whereas exposing the surface to oxygen or air plasma under oxidizing conditions results in a passive free radical-containing surface.

The method of coating the medicament-coated implant of this invention may be any appropriate well known coating technique, such as immersion coating, spray coating and the like, using a suitable solution or dispersion of the medicament dissolved or dispersed in an appropriate solvent or dispersant, such as water, ethanol, and the like, with the solvent not affecting the optics of the lens material. The coating solution or dispersion has a conventional concentration of medicament which corresponds to the particular coating technique selected. Typically, after the coating is applied to the implant, it is dried, for example, by drying at room temperature or above. The coating may be repeatedly applied, if necessary, to achieve the desired coating weight or thickness. The coating should not affect the transmission of visual light, and typically has a thickness in the range of from about $\frac{1}{100,000}$ mm to $\frac{1}{100}$ mm, and constitutes from about $\frac{1}{10,000}\%$ to about $\frac{1}{10}\%$ by weight of the implant.

Additional medicaments and other compounds may also be employed in conjunction with the compatible sulfated polysaccharide medicament coating of the present invention. For example, in one embodiment the coating is additionally complexed with antithrombin to provide the coated implant with anticoagulation properties.

While not wishing to be bound by any one theory, it is theorized that the coating of the refractive anterior chamber ocular implant with the above-specified polysaccharide medicament also fills the microscopic crevices that are present in the uncoated implant, even when polished to the greatest extent possible. Thus, the surface of the implant is rendered smoother and less adherent. In addition, the surface of the implant is softened, has its surface tension lowered, has its contact angle lowered, and becomes more inert, thereby reducing the potential for progressive endothelial loss. Thus, it is believed that the coating employed in accordance with this invention creates an enhanced "inert" state with respect to the minus power anterior chamber ocular implant, thereby rendering use of the present invention particularly advantageous in eyes which have had antecedent inflammation.

Moreover, it is theorized that the specified coating alters the abrasive potential of the implant and reduces the trauma associated with insertion and maintenance thereof. In addition, the specified coating may reduce the inflammatory potential of the implant and the dangerous sequelae resulting therefrom, including, among other effects, cataract formation. The coated implant may also act as a therapeutic agent to prevent and treat the untoward reactions to the implant previously described.

The following examples illustrate preferred embodiments of the implant of this invention. It will be understood that the following examples are merely illustrative, and are not meant to limit the invention in any way.

EXAMPLE 1

An uncoated minus power anterior chamber ocular implant in accordance with this invention and containing surface carboxyl groups is surface coated with low molecular weight heparin (i.e. about 2,000–5,300 daltons) by the following procedure. The carboxyl group-containing surface of the implant may preferably be made by initially incorporating about 5 weight per cent methacrylic acid into the monomer formulation used in preparing the implant. Alternatively, surface hydrolysis of pendant acrylate or methacrylate groups residing on the surface of the implant may be employed, in a manner well known to those skilled in the art. The pendant carboxylic acid groups on the surface of the implant are then reacted with a commercially available diamine, such as hexamethylene diamine or a polymeric diamine such as those commercially available under the JEFFAMINE series trade name from Texaco Chemical Company, in the presence of a water-soluble carbodimide coupling agent, to generate an amine grafted surface (through amide bond formation) where the non-attached portion of the amine resides as a free primary amine. To the free primary amine grafted surface is added the low molecular weight heparin that contains a terminal aldehyde group, and the aldehyde group is then coupled with the primary amine on the surface of the implant by a water-soluble carbodimide to yield a Schiff base, which is then reduced to give a secondary amine linkage to which is attached the low molecular weight heparin.

EXAMPLE 2

In another preferred embodiment, an uncoated minus power anterior chamber ocular implant in accordance with this invention and containing surface carboxyl groups, is obtained in accordance with Example 1. However, instead of reacting the surface carboxylic groups with a diamine, as in Example 1, an aldehyde-terminated heparin is first coupled with a diamine. This reaction utilizes an excess of diamine, such as a low molecular weight, water-soluble diamine, that reacts with the aldehyde-terminated heparin through one of its amine groups, generating an amido-bonded heparin derivatized with a free, pendant amino group. This water-soluble compound is then purified by dialysis to eliminate the excess, unreacted diamine, and the product obtained by lyophilization. The aminated heparin is then reacted with the hydrolyzed surface of the anterior chamber ocular implant through its surface carboxyl groups in the presence of a water-soluble carbodiimide coupling agent. In contrast to the previously described embodiment of Example 1, this process involves only one coupling reaction on the surface of the implant rather than two.

EXAMPLE 3

In yet another preferred embodiment, an uncoated minus power anterior chamber ocular implant in accordance with this invention is treated with a plasma in accordance with methods as previously described to generate an amine-containing surface, a carboxylic acid-containing surface, or an active or passive free radical-containing surface. If an amine-containing surface is obtained, aldehyde-terminated heparin may be employed to coat the surface of the implant in accordance with Example 1. If a carboxylic acid-containing surface is obtained, aminated heparin may be employed to coat the surface of the implant in accordance with Example 2. If an active or passive free radical-containing surface is obtained, amine or carboxylic acid-containing compounds of low or high molecular weight may be reacted with the surface to yield a covalently attached amine or carboxylic acid-containing implant surface, respectively, to which the designated aldehyde-terminated or aminated heparin compounds set forth in Examples 1 and 2, respectively, are employed to coat the surface of the implant with heparin. In a particularly preferred embodiment, the plasma treatment employed will act in such a manner as to permit trace surface moisture residing in the uncoated implant to be converted into passive free radical coupling agents via the formation of peroxide groups.

With respect to the foregoing examples, if anticoagulation properties are desired or wish to be increased, antithrombin may be added to complex with binding sites on the heparinized surface. Similarly, if additional ultraviolet radiation absorbing properties are desired, compounds having ultraviolet radiation absorbing properties such as compounds having benzotriazole groups, benzophenone groups, and mixtures thereof may be added into the monomer mixture to yield the minus power anterior chamber ocular implant to be coated with a compatible sulfated polysaccharide medicament in accordance with this invention.

This invention is also directed to a method of treating myopia comprising surgically implanting and anchoring in an anterior chamber of a phakic eye a minus power lens comprising at least one concave surface and a surface coating comprising a compatible sulfated polysaccharide medicament.

Again, while not wishing to be bound by any one theory, it is theorized that the present invention, wherein the coating is bonded to the implant surface as described herein, is advantageous over intraocular lenses which employ covalent attachment of heparin to a polyamine that is ionically adsorbed onto the lens surface, in that the coating of the present invention is less likely to be released and dissipated in the aqueous humor of the anterior and posterior chambers of the eye.

Although this invention has been illustrated by reference to specific embodiments, it will be apparent to those skilled in the art that various changes and modifications may be made which clearly fall within the scope of this invention.

What is claimed is:

1. A refractive anterior chamber ocular implant for placement in the anterior chamber of an eye having an anatomic lens in situ, the implant comprising a refracting lens, means for positioning the refracting lens in the anterior chamber of the eye to prevent contact between the implant and the anatomic lens, and a surface coating comprising a compatible sulfated polysaccharide medicament covalently bonded to the implant by end-group attachment.

2. An implant according to claim 1, in which the sulfated polysaccharide is selected from the group consisting of heparin, heparan sulfate, chondroitin sulfate, dermatan sulfate, chitosan sulfate, xylan sulfate, dextran sulfate, and sulfated hyaluronic acid.

3. An implant according to claim 2, in which the sulfated polysaccharide is heparin having a molecular weight in the range of about 2,500–15,000 daltons.

4. An implant according to claim 3, in which the heparin has a molecular weight in the range of about 2,500–10,000 daltons.

5. An implant according to claim 4, in which the heparin has a molecular weight in the range of about 2,500–5,300 daltons.

6. An implant according to claim 1, in which the coating has a thickness in the range of from about $1/100,000$ mm to $1/100$ mm.

7. An implant according to claim 1, in which the coating constitutes from about $1/10,000\%$ to about $1/10\%$ by weight of the implant.

8. An implant according to claim 1, in which the coating additionally comprises one or more compounds having anticoagulation properties.

9. An implant according to claim 8, in which the coating is additionally complexed with antithrombin.

10. An implant according to claim 1, in which the implant additionally comprises one or more compounds capable of absorbing ultraviolet radiation.

11. An implant according to claim 10, in which the ultraviolet radiation absorbing compound is selected from the group consisting of compounds having benzotrizole groups, benzophenone groups, and mixtures thereof.

12. A method of correcting refractive errors comprising surgically implanting and anchoring in an anterior chamber of an eye having an anatomic lens in situ an anterior chamber ocular implant comprising a refracting lens, means for positioning the refracting lens in the anterior chamber of the eye to prevent contact between the implant and the anatomic lens, and a surface coating comprising a compatible sulfated polysaccharide medicament covalently bonded to the implant by end-group attachment.

* * * * *

UNITED STATES PATENT AND TRADEMARK OFFICE
CERTIFICATE OF CORRECTION

PATENT NO. : 6,143,028
DATED : November 7, 2000
INVENTOR(S) : Galin et al.

It is certified that error appears in the above-identified patent and that said Letters Patent is hereby corrected as shown below:

Title page,
Item [56], References Cited, OTHER PUBLICATIONS,
Under "VMG Ferguson et al.," "follow" should read -- following --.
Under "VMG Ferguson et al.," "Opthamology" should read -- Ophthalmology --.
Under "The Eye", "Wstheimer" should read -- Westheimer --.
Under "Surface-modified IOL's", "IOL's" should read -- IOLs --.
Under "Surface-modified IOL's", "Uppala" should read -- Uppsala --.
Under "Minus Power", "Opthamology" should read -- Ophthalmology --.
Under "Heparin-modified", "Opthamology" should read -- Ophthalmology --.
Under "R. Larson et al.," "Surfact–" should read -- Surface– --.

Column 3,
Line 21, "heparin" (second occurrence) should read -- heparan --.

Column 4,
Line 55, "eve" should read -- eye --.

Column 6,
Line 9, "carbodimide" should read -- carbodiimide --.

Column 9,
Line 1, "carbodimide" should read -- carbodiimide --.

Signed and Sealed this

Thirteenth Day of July, 2004

JON W. DUDAS
*Acting Director of the United States Patent and Trademark Office*